United States Patent [19]

Rossetti et al.

[11] Patent Number: 4,507,499

[45] Date of Patent: Mar. 26, 1985

[54] N-(4-HYDROXYBENZYL)-3,4,5-TRIMETHOXYBENZAMIDE AND METHOD FOR PRODUCING TRIMETHOBENZAMIDE CHLOROHYDRATE

[75] Inventors: Vittorio Rossetti, Milan; Alessandro Dondoni, Ferrara; Giancarlo Fantin, Rovigo, all of Italy

[73] Assignee: Francis S.p.A., Caronno Pertusella, Italy

[21] Appl. No.: 413,554

[22] Filed: Aug. 31, 1982

[51] Int. Cl.³ .................. C07C 103/44; C07C 102/00
[52] U.S. Cl. ........................... 564/179; 564/176
[58] Field of Search ............................... 564/176, 179

[56] References Cited

U.S. PATENT DOCUMENTS 2,879,293  3/1959  Goldberg et al. .................. 564/176
3,083,140  3/1963  Testa ............................... 564/176 X
3,481,980  12/1969  Teitel et al. ....................... 564/176

OTHER PUBLICATIONS

March, *Advanced Organic Chemistry*, 2nd ed., pp. 378–379, McGraw-Hill.
Buehler et al., *Survey of Organic Syntheses*, p. 452, Wiley-Interscience.

*Primary Examiner*—Thomas A. Waltz
*Attorney, Agent, or Firm*—Oblon, Fisher, Spivak, McClelland & Maier

[57] ABSTRACT

The invention relates to a method for producing trimethobenzamide chlorohydrate.

According to such a method, a chloromethilation is carried out on anisle and, after reaction with urotropine followed by acidic hydrolisis, 4-methoxybenzylamide chlorohydrate is obtained which, demethyilated by hydrazoic acid, provides 4-hydroxy benzylamine chlorohydrated that, reacted with 3,4,5-trimethoxybenzoic acid chloride, provides N-(4-Hydroxybenzyl)-3,4,5-trimethoxybenzamide. The latter is per se a novel compound and is also the subject of the invention. This compound is reacted with sodium hydride and N,N-dimethylamino ethyl chloride to provide base trimethobenzamide, the latter being salified with hydrochloric acid.

1 Claim, No Drawings

N-(4-HYDROXYBENZYL)-3,4,5-TRIMETHOXYBENZAMIDE AND METHOD FOR PRODUCING TRIMETHOBENZAMIDE CHLOROHYDRATE

This invention relates to a method for producing trimethobenzamide chlorohydrate and a novel compound being developed during the process, which novel compound is N-(4-hydroxybenzyl)-3,4,5-trimethoxybenzamide.

Trimethobenzamide chlorohydrate is the commercial designation for N-[(2-dimethylaminoethoxy)benzyl]-3,4,5-trimethoxybenzamide chlorohydrate, which is a per se known compound and having pharmacological properties as antiemetic. It is a compound of formula

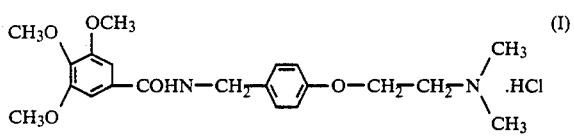

disclosed in U.S. Pat. No. 2,879,293, according to which it is obtained by catalytic reducing amination with hydrogen and Raney nickel of 4-(2-dimethylaminoethoxy)benzaldehyde and a pressure of about 70 kg/cm$^2$ and reaction with 3,4,5-trimethoxybenzoyl chloride. The above mentioned production method suffers from serious disadvantages, among which it would suffice to remind the danger in handling of the catalyst (which is inflammable at dry state), the need of using high pressures, and the use of complicated and quite expensive apparatus.

It is the primary object of the present invention to provide a method of producing trimethobenzamide chlorohydrate with high yields and which is of ready industrial applicability.

According to such a method, anisole is reacted at a temperature in the range of 10°-15° C. with hydrochloric acid gas and formaldehyde in water to provide a compound of formula

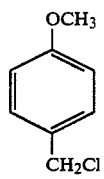

which is refluxed with urotropine in chlorinated solvent to provide the compound of formula

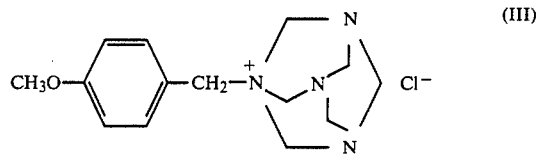

which is isolated by filtering and reflux reacted with hydrochloric acid in hydroalcohol solution, thus obtaining a compound of formula

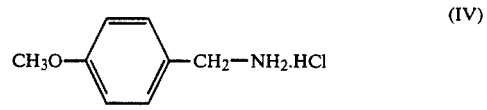

which, reflux reacted with aqueous hydrobromic or hydroiodic acid, provides a compound of formula

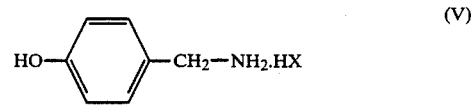

wherein X is Br or I, which is treated, in the presence of an inorganic base selected from the group comprising alkaline hydroxides, carbonates and bicarbonates, with 3,4,5-trimethoxybenzoic acid chloride to provide a compound of formula

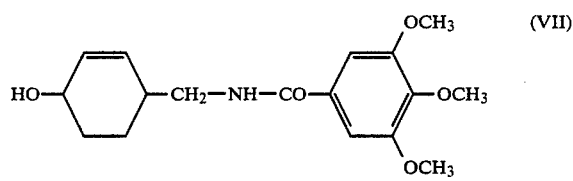

which is isolated and then treated, in the presence of alkaline hydroxides or hydrides, with N,N-dimethylamino ethylchloride, thus providing trimethobenzamide chlorohydrate.

The above described reaction scheme is ad follows:

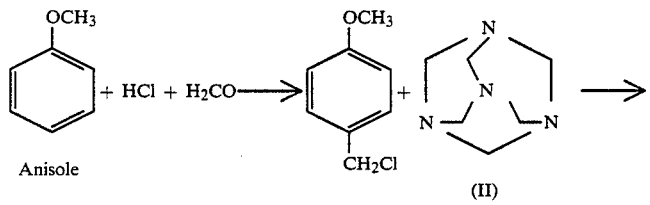

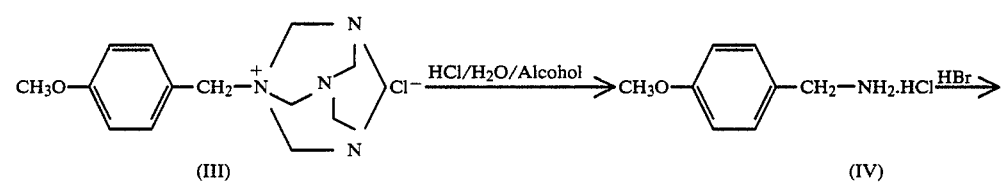

-continued

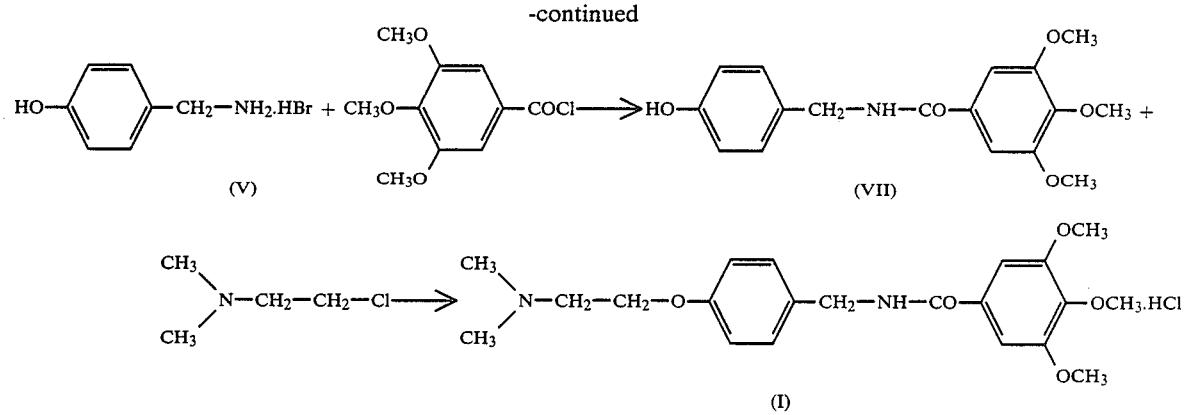

As the method according to the invention is carried, a novel compound is formed, the compound comprising N-(4-hydroxybenzyl)-3,4,5-trimethoxybenzamide of formula (VII) which in addition to being a useful intermediate could have interesting pharmacological characteristics.

In order that the method can be more clearly understood and define the characteristics of the novel compound we produced and isolated, some exemplary embodiments will now be given, embodiments which should not be intended as limiting of the scope of the present invention.

EXAMPLE 1

Preparation of N-(4-hydroxybenzyl)-3,4,5-trimethoxybenzamide of formula (VII)

13.5 g anisole are mixed with 11 ml 40% aqueous formaldehyde. The mixture is cooled to 10° C. and under stirring hydrochloric acid gas is bubbled for 3 hours, holding the temperature in the range of 10°–15° C. There is at the beginning the formation of a gelatinous white solid, which then disappears. The reaction is exothermic. Two phases are obtained; the excess of hydrochloric acid is neutralized by 40% sodium hydrate and extracted with dichloromethane. The organic extract is concentrated at reduced pressure and then vacuum distilled.

11.7 g 4-methoxybenzyl chloride of formula (II) (boiling temperature 115°–118° C./16 mmHg) are obtained (yield: 59.8%).

11.25 g methoxybenzyl chloride of formula (II) are dissolved in 30 ml chloroform (1,2-dichloroethane) and reated with 11 g urotropine. The reaction is exothermic. At the end of exothermicity, the mixture is reflux heated for 2 hours. The mixture is then cooled down to 0° C. and the obtained precipitate is filtered, washed with toluene and dried. 21 g adduct of formula (III) are obtained (m.p. 172°–175° C.; yield: 98%).

20 g product of formula (III) are reflux hydrolized in 300 ml methanol, 60 ml water and 66 ml concentrated hydrochloric acid for 30 minutes. The solvent is evaporated at reduced pressure, the residue is diluted with 200 ml water and, after alkalination with sodium hydrate, the product is extracted with 200 ml toluene. The toluene extract, dried on sodium sulphate, is concentrated to small volume at reduced pressure. The residual oil is treated with methanol and concentrated hydrochloric acid, the solvent is evaporated at reduced pressure and the residue, treated with acetone, provides 11.12 g 4-methoxy benzylamine chlorohydrate of formula (IV) (yield: 95%; m.p. 225°–230° C.) (In an exemplary embodiment, the toluene extract was directly used for the next reaction, providing the product of formula (V) with a yield of 95%).

10 g 4-methoxy benzylamine chlorohydrate of formula (IV) are reflux boiled for 4 hours with 16 ml hydrobromic acid 48% (d=1.47) (or 20 ml aqueous hydroiodic acid). The obtained solution is vacuum concentrated to dryness. The residue, treated with acetonitrile, provides 11.75 g (theorical yield, m.p. 175°–180° C.) 4-hydroxy benzylamine bromohydrate of formula (V) when HBr is used.

10 g 4-hydroxy benzylamine bromhydrate of formula (V) are dissolved in 200 ml water. 2 g sodium hydrate are added (or an equimolar amount of potassium hydrate) and 20 g sodium bicarbonate (or an equivalent amount of sodium carbonate or potassium carbonate). A suspension is obtained which, at a temperature of 20° C., is reacted with 162 ml of a 7% w/v toluene solution of 3,4,5-trimethoxybenzoic acid chloride.

The reaction mixture is stirred over one night at room temperature. The product is neutralized with diluted sulphuric acid and the precipitate is filtered and washed with water in the absence of sulphates. After drying, 15.1 g N-(4-hydroxybenzyl)-3,4,5-trimethoxybenzamide of formula (VII) are obtained (yield: 97%). The product, crystalized from N,N-dimethylformamide, provides the following analytical data:

I.R. (KBr): 3600 (NH), 1615 (C=O) cm$^{-1}$

H NMR (DMSO-d$_6$) (ppm, using tetramethylsilane as internal standard): 3.73 (s, 3H, OCH$_3$ [4]); 3.84 (S, 6H, OCH$_3$ [3,5]); 4.44 (d, 2H, CH$_2$, J=6.25 H$_z$) (a); [6.75 (d, 2H, ArH); 7.15 (d, 2H, ArH)](b); 7.28 (s, 2H, ArH); 8.9 (t, 1H, NH) (c); 9.25 (s, 1H, OH) (d).

MASS m/e: 317 (M+, 76) 197 (90), 195 (100), 168 (73), 153 (46), 122 (41), 107 (41)

m.p. 228°–230° C. (uncorrected) (a) with D$_2$O (48 hours contact) becomes singlet; (b) AA'BB' system centered at 6.95 ppm; (c) with D$_2$O (48 hours contact) disappears; (d) with D$_2$O (5 minutes contact) disappears.

Apparatus used:
I.R.: PERKIN-ELMER Mod. 297
NMR: BRUKER WP80 (80 MH$_z$)
MASS: VARIAN MAT 112
Melting point: Büchi (according to dr. Tottoli)

EXAMPLE 2

Preparation of N-[(2-dimethylaminoethoxy)benzyl]-3,4,5-trimethoxybenzamide chlorohydrate of formula (I)

2 g N-(4-hydroxybenzyl)-3,4,5-trimethodibenzamide of formula (VII) are dissolved in 20 ml N,N-dimethylformamide. 0.36 g sodium hydride are added (50% suspension in paraffine): hydrogen developes and the solution becomes green. The product is heated to 40°-50° C. and a solution of 0.75 g N,N-dimethylamino ethyl chloride in 30 ml toluene is added (obtained by suspension of 1 g N,N-dimethylamino ethyl chloride chlorohydrate in 30 ml toluene and treated with excess of 40% sodium hydrate). The product is reflux heated for 3 hours, then cooled, the salts are removed by filtering and the product is evaporated to dryness at reduced pressure. The residue, crystalized from toluene, is dissolved in isopropanol and, by addition of hydrochloric acid gas, the subject product precipitates which, filtered and dried, has a weight of 2.4 g (yield: 90%). The product obtained is consistent with British Pharmacopaea and United Stated Pharmacopaea.

Instead of using sodium hydride and N,N-dimethylformamide, as above disclosed, the sodium salt can be prepared in water and an equimolar amount of sodium hydrate, dry evaporate and carry out the reaction as above described in toluene only.

What is claimed is:

1. A method for producing trimethobenzamide chlorohydrate of formula:

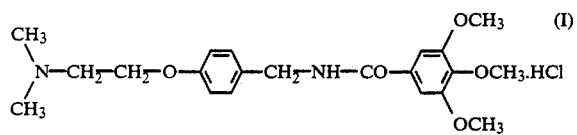

according to which anisole is reacted at a temperature in the range of 10°-15° C. with hydrochloric gas and formaldehyde in water to provide a compound of formula

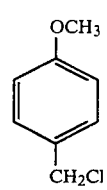

which is reflux treated with urotropine in a chlorinated solvent to provide a compound of formula

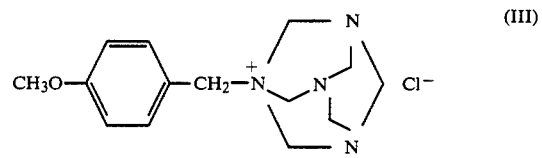

which is isolated by filtering and reflux reacted with hydrochloric acid in hydroalcohol solution, thus obtaining a compound of formula

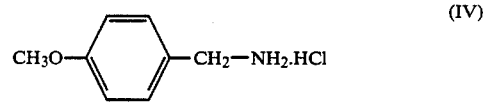

which reacted under reflux condition with aqueous hydrobromic or hydroiodic acid provides a compound of formula

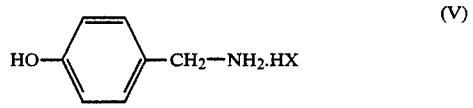

wherein X is Br or I, which is treated, in the presence of an inorganic base selected from the group comprising alkaline hydroxides, carbonates and bicarbonates, with 3,4,5-trimethoxybenzoic acid chloride to provide a compound of formula

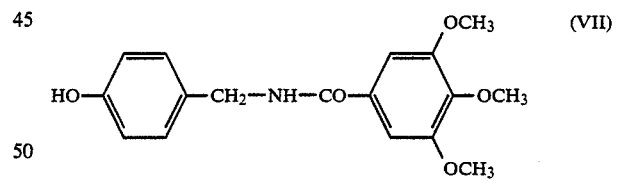

which is isolated and then treated, in the presence of alkaline hydroxides or hydrides, with N,N-dimethyamino ethyl chloride, thus obtaining trimethobenzamide chlorohydrate.

* * * * *